(12) United States Patent
Audoglio

(10) Patent No.: US 6,556,874 B2
(45) Date of Patent: Apr. 29, 2003

(54) ELECTRODE ARRANGEMENT

(75) Inventor: Roberto Audoglio, Linarolo (IT)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 0 days.

(21) Appl. No.: 09/794,110

(22) Filed: Feb. 27, 2001

(65) Prior Publication Data

US 2001/0020179 A1 Sep. 6, 2001

(30) Foreign Application Priority Data

Mar. 2, 2000 (DE) .......................... 100 11 572

(51) Int. Cl.$^7$ .............................................. A61N 1/362
(52) U.S. Cl. ...................................................... 607/126
(58) Field of Search ................................ 607/122, 125, 607/126, 127

(56) References Cited

U.S. PATENT DOCUMENTS

| 4,677,990 A | 7/1987 | Neubauer |
| 5,254,088 A | 10/1993 | Lundquist |
| 5,364,351 A | 11/1994 | Heinzelman |
| 5,376,109 A | 12/1994 | Lindegren |
| 5,423,884 A | 6/1995 | Nyman |
| 5,443,492 A | 8/1995 | Stokes |
| 5,476,500 A | 12/1995 | Fain |
| 5,531,783 A | 7/1996 | Giele |
| 5,571,162 A | 11/1996 | Lin |
| 5,683,447 A | 11/1997 | Bush |
| 5,693,081 A | 12/1997 | Fain |
| 5,728,140 A | 3/1998 | Salo |
| 5,755,764 A | * 5/1998 | Schroeppel .................. 607/127 |
| 5,871,532 A | 2/1999 | Schroeppel |
| 6,006,139 A | 12/1999 | Kruse |

FOREIGN PATENT DOCUMENTS

| DE | 30 27 587 A1 | 12/1981 |
| DE | 35 07 119 A1 | 8/1986 |
| DE | 195 46 941 A1 | 6/1997 |
| EP | 0 212 955 A2 | 3/1987 |
| EP | 0 656 218 A1 | 6/1995 |
| EP | 0 667 126 A1 | 8/1995 |
| WO | WO 99/53993 A1 | 10/1999 |

* cited by examiner

Primary Examiner—Gregory Wilson
(74) Attorney, Agent, or Firm—Hahn Loeser + Parks LLP; Stephen L. Grant

(57) ABSTRACT

An electrode arrangement provides an electrode line (10) carrying at least a first fixing element (16) which is designed to fix the electrode line to body tissue, especially the myocardium of a heart, and which is arranged at a spacing relative to the distal end (12) of the electrode line (10), wherein the first fixing element (16) is fixedly connected to the electrode line (10) and has a free first end (40) which has a component of extension in a direction tangential with respect to the electrode line (10) and which is of such a configuration that the first fixing element (16) penetrates into body tissue that is adjacent to the electrode line in the situation of use by a rotary movement of the electrode line (10) about the longitudinal axis thereof.

26 Claims, 3 Drawing Sheets

ELECTRODE ARRANGEMENT

The invention relates to an electrode arrangement comprising an electrode line carrying at least a first fixing element which is designed to fix the electrode line to body tissue, in particular the myocardium of a heart, and which is arranged at a spacing relative to the distal end of the electrode line.

The invention further relates to an electrode line having electrodes for the stimulation of the myocardium of a human heart or for picking up electrical signals from a human heart. Electrode lines of that kind are used in particular in connection with an implanted cardiac pacemaker which provides artificial stimulation by way of the electrodes of the electrode line.

BACKGROUND OF THE ART

An aspect of particular interest is, inter alia, stimulation of the septum between the left and right ventricles of the heart. Electrode arrangements for septum stimulation are known for example from German application 195 46 941, and U.S. Pat. Nos. 5,728,140, 5,683,447, 5,476,500 and 5,693,081. None of those electrode lines satisfactorily permits bi-phase stimulation of the upper septum. Anchorage of the electrode line in the septum is also not satisfactorily achieved with the known electrode arrangements.

Having regard to the background of the state of the art, the object of the invention is to afford an alternative electrode arrangement which as far as possible avoids the described disadvantages of the state of the art.

SUMMARY OF THE INVENTION

In accordance with the invention, this object is attained by an electrode arrangement of the kind set forth in the opening part of this specification, in which the first fixing element is fixedly connected to the electrode line and has at least one free end extends tangentially outwardly from the electrode line and that is configured so that the first fixing element penetrates body tissue by a rotary movement of the electrode line about its longitudinal axis thereof.

An electrode arrangement of that kind advantageously manages without fixing means which are movable relative to the electrode line, as are known from U.S. Pat. Nos. 5,476,500, 5,683,447 and 5,693,081.

In one embodiment, the first fixing element is in the form of a helical coil that is rigidly connected to the electrode line so that the helical coil extends around the electrode line substantially coaxially at a spacing relative to the electrode line. The first fixing element is thus of a corkscrew-like configuration and is rigidly connected to the electrode line. By virtue of rotary movement of the electrode line about the longitudinal axis thereof, the free end of the fixing element hooks into adjacent body tissue and thus provides for secure fixing of the electrode line to the body tissue. That permits in particular active fixing to the septum of a heart. In that arrangement the turns of the coil are preferably at a uniform spacing from each other, like also the turns of a corkscrew. In addition the free end of the fixing element is preferably sharpened to a point.

The first fixing means is preferably fixed with its distal end to the electrode line so that the free end of the first fixing means is closer to the proximal end of the electrode line. In conjunction with a second fixing element which is coiled in a corkscrew-like fashion, with an opposite direction of rotation, at the distal end of the electrode line, it is possible, as described hereinafter, to avoid loading the electrode line when the myocardium contracts.

In another embodiment, the first fixing element has a second free end which with respect to the electrode line involves the same tangential orientation as the first free end, but an opposite axial orientation, with the first fixing element fixed to the electrode line between both free ends. This central fixing of the first fixing element to the electrode line with two free ends has the advantage, by virtue of the oppositely directed directions of rotation of the two resulting helix portions, that, when the helix portions are screwed into adjacent tissue, a certain stressing of the two free ends relative to each other occurs. That stressing effect results in secure fixing of the securing action which otherwise can rather be released by unintentional rotational movements.

In most embodiments, the electrode element carries a second fixing element at its distal end. Such an electrode arrangement can be actively fixed to the body tissue at two locations, more specifically at its distal end and at a spacing therefrom, so that the two fixing elements also assume a fixed position relative to each other, with respect to the body tissue.

In that arrangement the second fixing element is also of a corkscrew-like configuration in the form of a helical coil with a free end, wherein the second fixing element involves a direction of rotation opposite to the first fixing element. Even if the second fixing element is rigidly connected to the electrode line, the electrode line can be rotated from its proximal end about the longitudinal axis thereof in order in that way to cause both fixing elements to penetrate into adjacent body tissue in the same direction. As a consequence of the opposite directions of rotation of the two fixing elements and the measure, which is directly related thereto, of fixing the first fixing element with its distal end to the electrode line, the myocardium is upset between the two fixing elements when they are screwed in. This avoids high levels of loading on the electrode line in the event of contraction of the myocardium.

Instead of the second fixing element being rigidly connected to the electrode line in such a way that the second fixing element, like the first fixing element, also rotates with the electrode line, it is also possible to provide a drive for the second fixing element, which makes it possible for the second fixing element to be driven with a rotational movement about the longitudinal axis of the electrode line, independently of the electrode line, more particularly preferably from the proximal end of the electrode line. Preferably the first fixing element is connected to the electrode line while the second fixing element is rotatable with respect to the electrode line by means of a bar which is introduced in the electrode line. That kind of drive is known per se for actively fixable screw electrodes at the distal end of the electrode line.

In one embodiment, the electrode arrangement is one which has a first electrode with an electrically conductive surface on the surface of the electrode line, which is adjacent to the free end of the first fixing element. This arrangement of the first electrode relative to the first fixing element ensures intensive contact of the first electrode with the body tissue in the long term. In that case the first fixing element is preferably electrically conductively connected to the first electrode and in that way itself becomes a component part of the first electrode. The first electrode moreover is usually formed by the surface of the electrode line, around which the first fixing element passes.

In most embodiments, the electrode arrangement has at least one second electrode at its distal end. A second electrode of that kind, in particular in the immediate proximity of the second fixing element which is usually part of the second electrode, permits the delivery of bipolar and in particular bi-phase stimulation pulses to the body tissue. In that respect, the bi-phase stimulation pulses can overlap in respect of time.

One particular embodiment of an electrode arrangement includes precisely two fixing elements which are in the form of corkscrew-like helical coils, which are each provided with a free end adapted to penetrate into tissue and which are arranged on the one hand at the distal end of the electrode line and on the other hand remote therefrom, and at least two electrodes with an electrically conductive surface, which are respectively arranged in the immediate proximity of the fixing means. An electrode arrangement of that kind advantageously permits bi-phase stimulation of the high septum of a heart.

Such an embodiment of an electrode line further includes two coaxial, electrically conductive coils which are electrically insulated relative to each other and with respect to the exterior of the electrode line and of which the outer coil contacts the first electrode which is remote from the distal end of the electrode line while the inner coil contacts the electrode at the distal end of the electrode line. An electrode line of that kind has a high level of flexibility without the danger of the electrically conductive coils breaking. In addition an electrode line of that kind represents secure contacting of the electrodes.

Most embodiments of the electrode line will also have control means with which the distal end can be deflected in the bilateral direction in per se known manner. That permits the targeted guidance of the electrode line to its target location. Control means of that kind are known for example from U.S. Pat. Nos. 5,254,088, 5,364,351, 5,376,109 and 5,423,884, as well as European published application 0 667 126 and German application 35 07 119.

BRIEF DESCRIPTION OF THE DRAWINGS

The invention will now be described in greater detail by means of an embodiment with reference to the Figures in which identical parts are identified by identical reference numerals and in which.

DETAILED DESCRIPTION OF THE INVENTION

Figure 1:
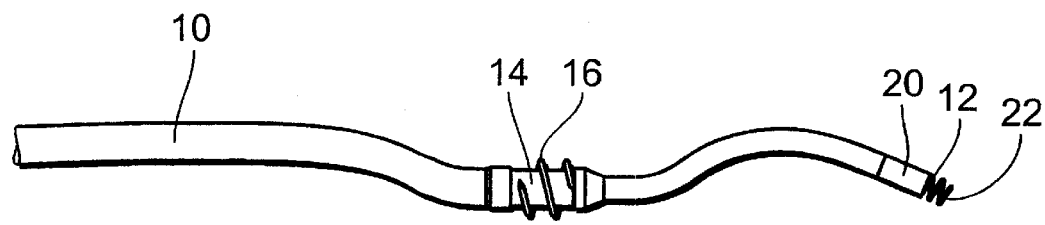
FIG. 1 is a simplified external view of the distal region of an electrode line according to the invention.

FIG. 1 shows that part of an electrode line 10 that adjoins the distal end 12 thereof. Provided at a spacing from the distal end 12 of the electrode line 10 are a first electrode 14 and a first fixing element 16. The first fixing element 16 is rigidly fixed to the electrode line 10 and extends around the electrode line 10 in a corkscrew-like manner at a spacing relative to the electrode line 10. The region of the electrode line 10 that is embraced by the fixing element 16 is in the form of the first electrode 14 and has an electrically conductive surface. This is in electrical contact with the first fixing element 16 so that the first fixing element 16 is part of the first electrode 14.

Figure 2A:
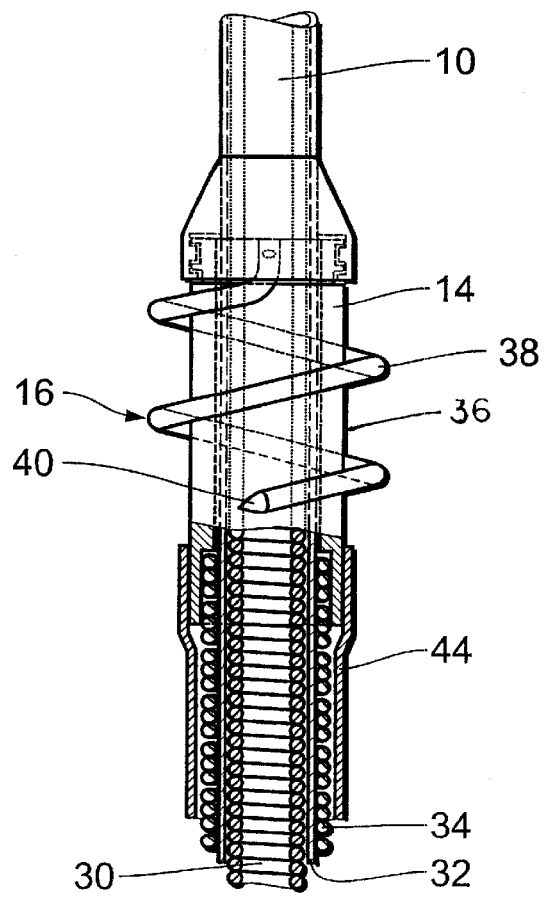
FIG. 2a is a sectional view through the electrode line of FIG. 1 in the region of a fixing element which is remote from the distal end of the electrode line.

As best illustrated in FIG. 2a, the first fixing element 16 is fixed to the distal end of the first electrode 14 so that a pointed free end 40 of the first fixing element 16 is disposed in the proximity of the proximal end of the first electrode 14. This arrangement has the advantage of avoiding problems such as hooking engagement of the free end 40 of the first fixing element 16 upon insertion of the electrode line 10 for example into a human heart.

A second electrode 20 is provided in the form of a tip electrode at the distal end 12 of the electrode line 10. Also fixed to the distal end 12 is a second fixing element 22 which is also formed by a metal wire which is shaped in a corkscrew-like fashion and the free end of which can be screwed into the myocardium of a heart for active fixing therein. To accomplish that, the entire electrode line 10 is rotated about its longitudinal axis. The second fixing element 22 is also connected to the second electrode 20 in such a way that the second fixing element 22 becomes a component part of the second electrode. The second electrode 20 is moreover formed by an electrically conductive surface of the electrode line 10 at the distal end 12 thereof.

FIG. 2a shows in detail the region of the first electrode 14 and the first fixing element 16 of the electrode line 10. As one of the basic components of the electrode line 10, it is possible to see an inner wire coil 30 which is surrounded by a tubular silicone insulation 32 and which leads to and electrically contacts the tip electrode 20.

Starting from the proximal end of the electrode line 10 towards the first electrode 14 the silicone insulation 32 is surrounded by a second wire coil 34 which coaxially surrounds the inner wire coil 30 and the tubular silicone insulation. At its distal end the outer wire coil 34 contacts the first electrode 14 formed by a metal sleeve 36 which coaxially encloses the inner wire coil 30 and the tubular silicone insulation 32.

The metal sleeve 36 forming the first electrode 14 is connected to one end of a metal helix 38 wound in a corkscrew-like configuration, with the distal end of the metal sleeve 36, fixedly, for example by welding. The corkscrew-like metal helix 38 forms the first fixing element 16 and is so shaped that the turns of the metal helix wind around the metal sleeve 36 at a spacing from each other and relative to the metal sleeve 36. The metal helix 38 has a substantially tangentially oriented, pointed free end 40 which projects freely into space and which can penetrate into adjacent body tissue by virtue of rotation of the entire electrode line 10 about its longitudinal axis. The pointed free end 40 is disposed in the proximity of the proximal end of the first electrode 14.

The metal helix 38 is so designed that the free end 40 penetrates into the adjacent myocardium by virtue of rotation of the electrode line 10 in the counterclockwise direction and in that way brings the myocardium into close contact with the first electrode 14. For example two and a half revolutions of the electrode line are required for that purpose. The metal helix 38 accordingly has two turns and extends over about 80% of the length of the first electrode 14. The selected configuration and fixing of the metal helix 38 further has the effect that, when the first fixing element 16 is screwed in, the myocardium is pushed in the direction of the tip electrode 22 so that, as it were, the myocardium is upset somewhat between the two electrodes. That reduces a loading on the electrodes and the electrode line during myocardium contraction.

To remove the electrode line it only needs to be rotated about its own axis in the clockwise direction in order to screw the two fixing means 16 and 22 out of the myocardium.

The outer wire coil 34 is surrounded by an outer tubular silicone insulation 44. This means that the electrode arrangement has precisely two outwardly electrically operative components that are formed on the one hand by the tip electrode 20 and the second fixing element 22 and on the other hand by the metal sleeve 36 and the metal helix 38.

While not specifically shown in the drawings, control or guide wires in the interior of the electrode line serve in known manner for controlling and guiding the electrode line by lateral deflection of the distal end 12 of the electrode line.

Figure 2B:
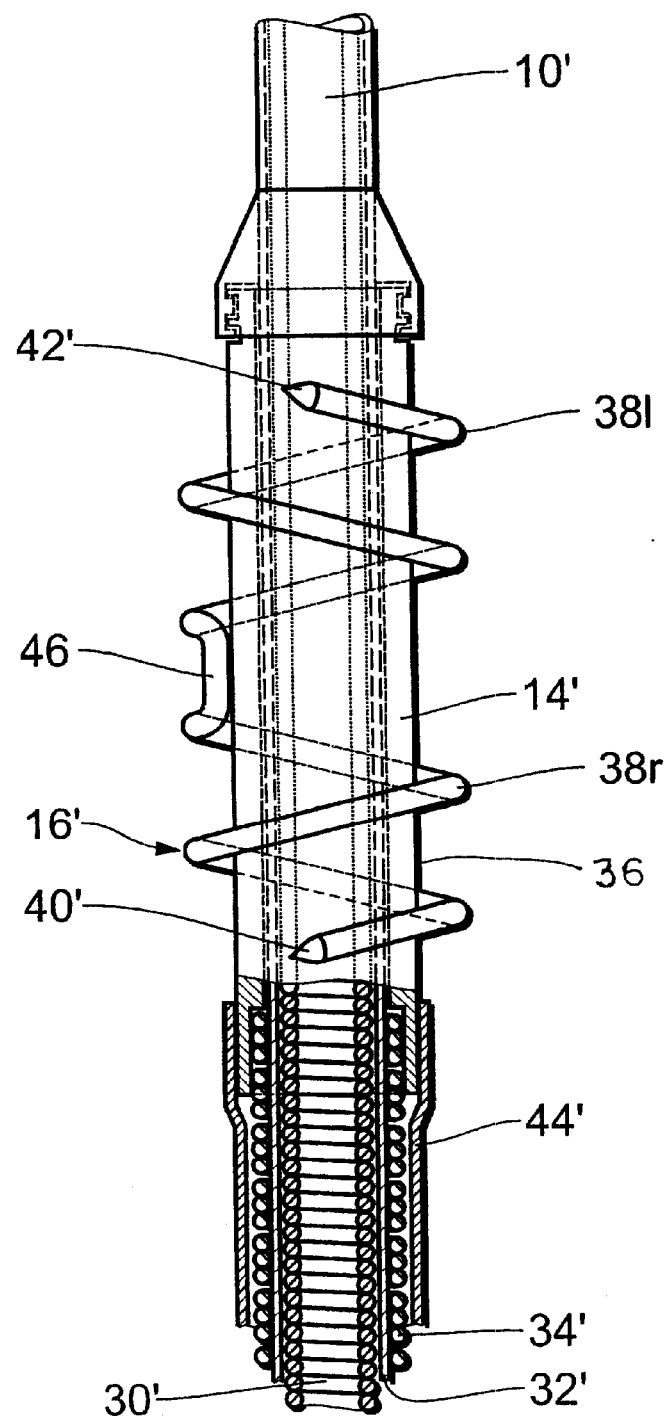
FIG. 2b shows an alternative embodiment of the fixing element of FIG. 2a, and FIG. 3 is a representation of a human heart in section with an electrode line in place.

FIG. 2b shows a second embodiment 16' of the first fixing element, which differs from the fixing element 16 shown in FIG. 2a because the alternative fixing element 16' has two pointed free ends 40' and 42'. The two free ends 40' and 42' are disposed at the ends of two oppositely directed metal helices 38r and 38l of which the metal helix 38r is right-handed while the metal helix 38l is left-handed. The two metal helices 38r and 38l extend from a central portion 46 of the fixing element 16', which is welded to the electrode 14' to fix the first fixing element 16' to the electrode 14'. The first fixing element 16' is thus connected to the electrode 14' centrally between its two free ends 40' and 42'. If the fact that the metal helix 38l is left-handed is disregarded, the metal helices 38l and 38r correspond to the metal helix 38 in FIG. 2a. When the metal helices 38l and 38r are screwed into adjacent body tissue the metal helices 38l and 38r are braced in relation to each other and thereby afford secure fixing of the first fixing element 16' in the body tissue.

Figure 3:
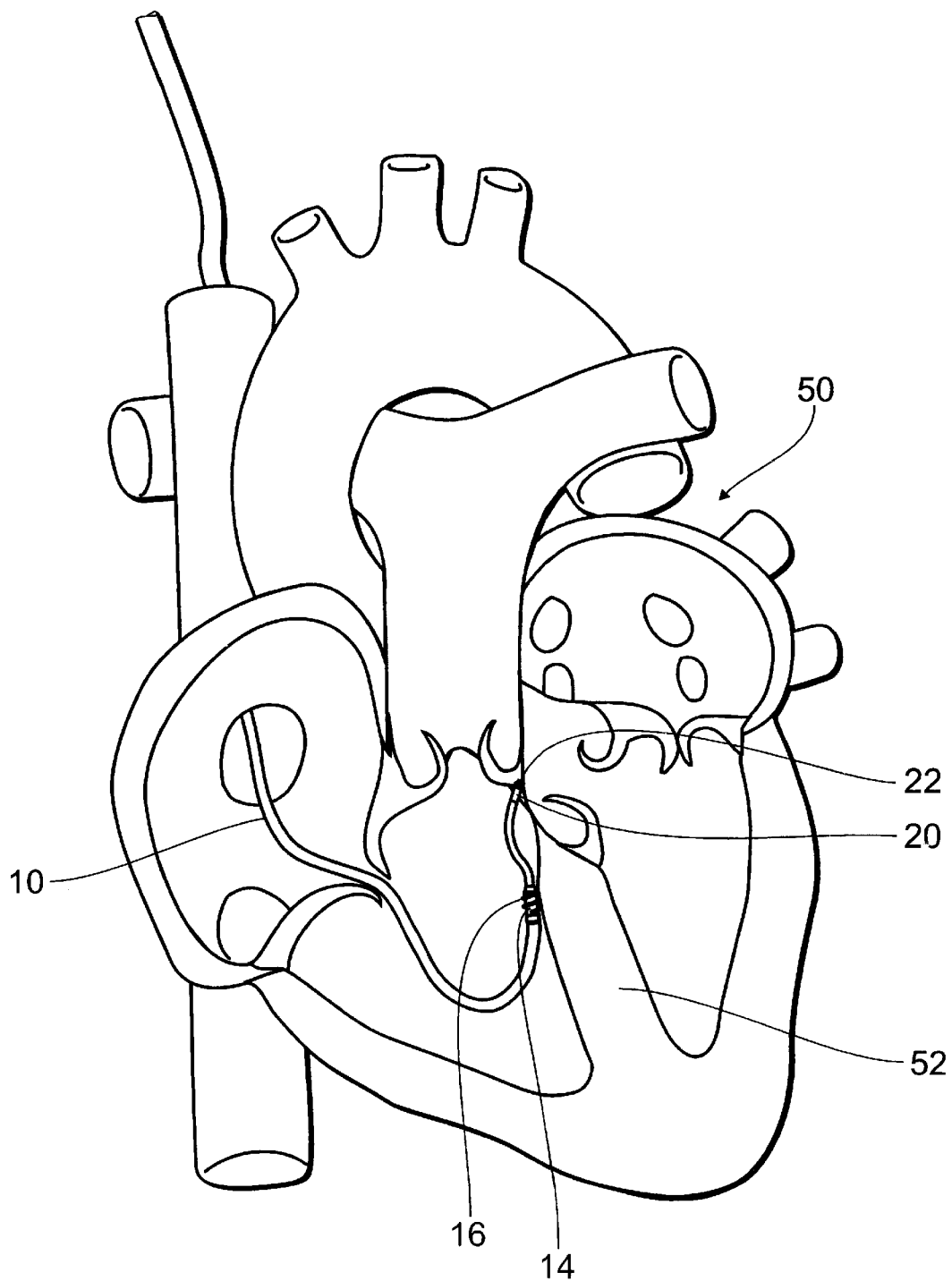

FIG. 3 shows a sectional view of a human heart 50 into which the electrode line 10 with the first electrode 14 and the second electrode 20 is introduced so that the tip electrode 20 bears against the high septum 52 and the first electrode 14 also bears against the septum 52 at a predetermined spacing relative to the second electrode 20. Both fixing elements 16 and 22 are screwed into the septum 52 by axial rotation of the electrode line 10 about the longitudinal axis thereof.

A particular advantage of the illustrated electrode arrangement is that it permits bi-phase stimulation of the high septum with pulses that overlap in respect of time, which is a possible alternative to biventricular stimulation for patients with a prolonged interventricular conduction time.

To accomplish this, the electrode line 10 is connected at its proximal end to a per se known implantable cardiac pacemaker which separately contacts the inner and the outer coils 30 and 34 so that electrical pulses can be delivered to the first electrode 14 and the second electrode 20 independently of each other.

The specific configuration of the two fixing elements 16 and 22 permits active fixing of the electrode line at two locations on the septum 52, wherein the distal end 12 of the electrode line 10 is fixed directly to the stem of the pulmonary artery in the high septum while the first fixing element 16 engages somewhat spaced therefrom but still into the high septum. The arrangement shown in FIG. 3 of the first and second electrodes 14 and 20 as well as the first and second fixing elements 16 and 22 predetermines both the configuration of the fixing elements 16 and 22 and also the spacing of the electrodes 14 and 20 as well as that of the corresponding fixing elements 16 and 22 on the electrode line 10.

Tests have shown that such an arrangement makes it possible to produce a double depolarisation front which involves the entire region of the septum 52 of the heart if both cathodic and also anodic pulses, that is to say two pulses in phase opposition, are delivered into a limited region of the interventricular septum, that region being about 2 centimeters in size and directly adjoining the entrance of the pulmonary artery into the ventricle. In that situation the depolarisation front emanating from the cathodic electrode moves from the surface to the interior of the septal myocardium while the depolarisation front emanating from the anodically actuated electrode moves from the interior of the myocardium to the surface thereof. In that respect the depolarisation effect follows the natural conduction paths which extend within the septum so that a delay in interventricular activation is avoided, as occurs with the usual stimulation at the apex of the right ventricle. That restores the natural physiological dynamics of contraction of the heart.

An important factor in this respect is the intensive contact of the electrodes with the myocardium, which is ensured by the above-described embodiment of the electrode. That is made possible by the active fixing action by means of the described fixing means which are both of an electrically conductive nature and conductively connected to the electrodes so that they themselves become a component part of the electrodes.

What is claimed is:

1. An electrode arrangement, comprising:
an electrode line with at least a first element for fixing the electrode line to body tissue, the first fixing element being spaced apart from a distal end of the electrode line, wherein the first fixing element is fixedly connected to the electrode line and has a free end that extends tangentially outwardly from the electrode line, the first fixing element being configured to penetrate into the body tissue that is adjacent to the electrode line when the electrode line is rotated about a longitudinal axis thereof, the first fixing element having at least one portion that is wound in a helical coil-like manner around the electrode line substantially coaxially at a spacing therefrom and which is rigidly connected thereto.

2. The electrode arrangement of claim 1 wherein the first fixing element has turns spaced from each other in the longitudinal direction of the electrode line.

3. The electrode arrangement of claim 2 wherein the free end of the first fixing element is pointed.

4. The electrode arrangement of claim 1 wherein the first fixing element has a second free end has the same tangential orientation to the electrode line as the first free end but an opposite axial orientation, with the first fixing element fixedly connected to the electrode line between the first and second free ends.

5. The electrode arrangement of claim 1, further comprising a second fixing element, located at the distal end of the electrode line.

6. The electrode arrangement of claim 5, wherein the second fixing element is connected to the electrode line such that said second fixing element is rotatably drivable together with the electrode line by rotation of the electrode line about its longitudinal axis.

7. The electrode arrangement of claim 5 wherein the second fixing element comprises a helical coil with a free end and a direction of rotation that is opposite to that of the first fixing element.

8. The electrode arrangement of claim 7 further comprising a second electrode arranged at the distal end of the electrode line.

9. The electrode arrangement of claim 8 wherein the first and second fixing elements each comprise a helical coil with the free end thereof adapted to penetrate into tissue and which are arranged so that one fixing element is at the distal end of the electrode line and the other fixing element is remote therefrom, with at least one electrode having an electrically conductive surface in the immediate proximity of the respective first and second fixing elements.

10. The electrode arrangement of claim 8, further comprising a first and a second coaxial electrically conductive coil, electrically insulated from each other, such that the first coil contacts the first electrode and the second coil contacts the second electrode.

11. The electrode arrangement of claim 10, wherein the first coil is located radially outwardly from the second coil.

12. The electrode arrangement of claim 10, further comprising a control means in an interior of the electrode line, such that the distal end thereof is laterally deflectable into a selectable direction from the proximal end of the electrode line.

13. The electrode arrangement of claim 1 further comprising a first electrode with an electrically conductive surface on the surface of the electrode line, said first electrode positioned adjacent to the free end of the first fixing element.

14. The electrode arrangement of claim 13 wherein the first electrode is formed from the surface of the electrode line, around which the first fixing element extends.

15. The electrode arrangement of claim 14 wherein the first fixing element is electrically conductive and is electrically connected to the first electrode such that the first electrode and the first fixing element act jointly for the delivery of electrical pulses or for picking up electrical signals.

16. The electrode arrangement of claim 15 wherein the first fixing element is fixed to the electrode line in the region of a distal end of the first electrode while the first free end of the first fixing element is disposed in the region of a proximal end of the first electrode.

17. The electrode arrangement of claim 1 wherein the free end of the first fixing element is pointed.

18. An electrode arrangement, comprising:
  an electrode line with at least a first element for fixing the electrode line to body tissue,
  the first fixing element being spaced apart from a distal end of the electrode line,
  wherein the first fixing element is fixedly connected to the electrode line and has a first and a second free end, each of which extends tangentially outwardly from the electrode line, the first fixing element being configured to penetrate into the body tissue that is adjacent to the electrode line when the electrode line is rotated about a longitudinal axis thereof, the first and second free ends having opposite axial orientations, with the first fixing element fixedly connected to the electrode line between the first and second free ends.

19. The electrode arrangement of claim 18, further comprising a second fixing element, located at the distal end of the electrode line.

20. The electrode arrangement of claim 19, wherein the second fixing element is connected to the electrode line such that said second fixing element is rotatably drivable together with the electrode line by rotation of the electrode line about its longitudinal axis.

21. The electrode arrangement of claim 19, wherein the second fixing element is connected to a drive such that said second fixing element is rotatably drivable about the longitudinal axis of the electrode drive, independently of the electrode line.

22. The electrode arrangement of claim 19 wherein the second fixing element comprises a helical coil with a free end and a direction of rotation that is opposite to that of the first fixing element.

23. The electrode arrangement of claim 18 further comprising a first electrode with an electrically conductive surface on the surface of the electrode line, said first electrode positioned adjacent to the free end of the first fixing element.

24. The electrode arrangement of claim 23 wherein the first electrode is formed from the surface of the electrode line, around which the first fixing element extends.

25. The electrode arrangement of claim 18 wherein the free end of the first fixing element is pointed.

26. The electrode arrangement of claim 18, wherein the first fixing element has turns spaced from each other in the longitudinal direction of the electrode line.

* * * * *